(12) United States Patent
Tsujita et al.

(10) Patent No.: US 11,331,250 B2
(45) Date of Patent: May 17, 2022

(54) METHOD FOR MANUFACTURING COLORED SHEET AND COLORED SHEET

(71) Applicant: Panasonic Intellectual Property Management Co., Ltd., Osaka (JP)

(72) Inventors: Kazuma Tsujita, Hyogo (JP); Takao Kajima, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 194 days.

(21) Appl. No.: 16/332,388

(22) PCT Filed: Feb. 17, 2017

(86) PCT No.: PCT/JP2017/005876
§ 371 (c)(1),
(2) Date: Mar. 12, 2019

(87) PCT Pub. No.: WO2018/061242
PCT Pub. Date: Apr. 5, 2018

(65) Prior Publication Data
US 2020/0085699 A1 Mar. 19, 2020

(30) Foreign Application Priority Data
Sep. 27, 2016 (JP) .............................. JP2016-187859

(51) Int. Cl.
*B41J 2/21* (2006.01)
*A61Q 1/02* (2006.01)
(Continued)

(52) U.S. Cl.
CPC .............. *A61K 8/0208* (2013.01); *A61Q 1/02* (2013.01); *B41J 2/211* (2013.01); *B41M 1/26* (2013.01);
(Continued)

(58) Field of Classification Search
CPC .... A61K 8/0208; A61K 8/0245; A61K 8/025; A61Q 1/02; A61Q 19/08; B41J 2/211;
(Continued)

(56) References Cited

U.S. PATENT DOCUMENTS

2006/0211572 A1 9/2006 Yukawa
2009/0032054 A1 2/2009 Griffiths et al.
(Continued)

FOREIGN PATENT DOCUMENTS

CN 101932437 12/2010
CN 104814885 8/2015
(Continued)

OTHER PUBLICATIONS

International Search Report of PCT application No. PCT/JP2017/005876 dated May 16, 2017.
(Continued)

*Primary Examiner* — Lamson D Nguyen
(74) *Attorney, Agent, or Firm* — Wenderoth, Lind & Ponack, L.L.P.

(57) ABSTRACT

A method for manufacturing a colored sheet for coloring an object by adhesion to the object includes, a coloring step of applying by spraying, a first coating fluid containing first microparticles for coloring to a thin film of a print receiver body which has a sheet-shaped support body and the thin film, the thin film being peelably held on the sheet-shaped support body to serve as a base material of an adhesive sheet which is to be adhered to the object, and a restricting step of applying by spraying, before the coloring step, a second coating fluid for restricting the first microparticles from penetrating the thin film to a location where the first coating fluid is to be applied.

5 Claims, 5 Drawing Sheets

(51) Int. Cl.
  *B41M 1/26* (2006.01)
  *A61K 8/02* (2006.01)
  *B41M 5/00* (2006.01)
(52) U.S. Cl.
  CPC ........ *B41M 5/0017* (2013.01); *B41M 5/0047* (2013.01); *B41M 5/0088* (2013.01)
(58) Field of Classification Search
  CPC .... B41M 1/26; B41M 5/0017; B41M 5/0047; B41M 5/0088
  See application file for complete search history.

(56) References Cited

U.S. PATENT DOCUMENTS

| | | |
|---|---|---|
| 2009/0060856 A1 | 3/2009 | Katsuyama et al. |
| 2011/0117174 A1 | 5/2011 | Kergosien et al. |
| 2015/0265030 A1 | 9/2015 | Kusukame et al. |

FOREIGN PATENT DOCUMENTS

| | | |
|---|---|---|
| JP | 52-097225 | 8/1977 |
| JP | 58-163297 U | 10/1983 |
| JP | 2-031581 U | 2/1990 |
| JP | 9-156204 | 6/1997 |
| JP | 2009-282064 A | 12/2009 |
| JP | 2015-193604 | 11/2015 |
| JP | 2016-027027 | 2/2016 |
| WO | 2006/101122 | 9/2006 |

OTHER PUBLICATIONS

The Extended European Search Report dated Aug. 20, 2019 for the related European Patent Application No. 17855201.4.

English Translation of Chinese Search Report dated Jun. 30, 2021 for related Chinese Patent Application No. 201780058447.6.

METHOD FOR MANUFACTURING COLORED SHEET AND COLORED SHEET

CROSS-REFERENCE TO RELATED APPLICATIONS

This application is a U.S. national stage application of the PCT International Application No. PCT/JP2017/005876 filed on Feb. 17, 2017, which claims the benefit of foreign priority of Japanese patent application 2016-187859 filed on Sep. 27, 2016, the contents all of which are incorporated herein by reference.

TECHNICAL FIELD

The present disclosure relates to a colored sheet that is adhered to an object to color the object, and to a method for manufacturing the colored sheet.

BACKGROUND ART

Such a conventional colored sheet has been proposed that is adhered to human skin to hide freckles or wrinkles. For example, PTL 1 discloses a colored thin film that is adhesive to skin and can prevent unnatural appearance after it has been adhered to skin.

CITATION LIST

Patent Literature

PTL 1: Unexamined Japanese Patent Publication No. 2016-27027

SUMMARY

A colored sheet manufacturing method in accordance with the present disclosure is a method for manufacturing a colored sheet for coloring an object by adhesion to the object, and includes: a coloring step of applying by spraying, a first coating fluid containing first microparticles for coloring to a thin film of a print receiver body which has a sheet-shaped support body and the thin film, the thin film being peelably held on the sheet-shaped support body to serve as a base material of an adhesive sheet which is to be adhered to the object; and a restricting step of applying by spraying, before the coloring step, a second coating fluid for restricting the first microparticles from penetrating the thin film to a location where the first coating fluid is to be applied.

A colored sheet in accordance with the present disclosure is a colored sheet for coloring an object by adhesion to the object, and includes: a sheet-shaped support body; a thin film that is peelably held on the sheet-shaped support body and serves as a base material of an adhesive sheet which is to be adhered to the object; a restriction layer that is disposed on the thin film and contains spherical microparticles; and a colored layer that is disposed on the restriction layer and contains a larger number of acicular microparticles than a number of acicular microparticles contained in the restriction layer.

DESCRIPTION OF EMBODIMENTS

The colored sheet adhered to an object to color the object is preferably thin and flexible to prevent unnatural appearance when it is adhered to an object. It is relatively easy to apply an ink to a thin film, which is a base material of such colored sheet. However, we have found that, in a case where the thin film is colored using the inkjet technique or the like to have a size and a color individually corresponding to a surface condition of the object to which the thin film will be adhered, the coating fluid penetrates to the back surface of the thin film or causes color bleeding.

It is an object of the present disclosure to solve this problem and to provide a method for manufacturing a colored sheet that can color a surface of a thin film in an arbitrary color. It is another object of the present disclosure to provide such colored sheet.

EXEMPLARY EMBODIMENT

Hereinafter, an exemplary embodiment will be described with reference to the accompanying drawings as appropriate. However, unnecessarily detailed description may occasionally be omitted. For example, detailed description of well-known matters and redundant description of substantially the same configuration may occasionally be omitted. This is to avoid the following description from becoming unnecessarily redundant, and to allow any person skilled in the art to easily understand the description.

Figure 1:
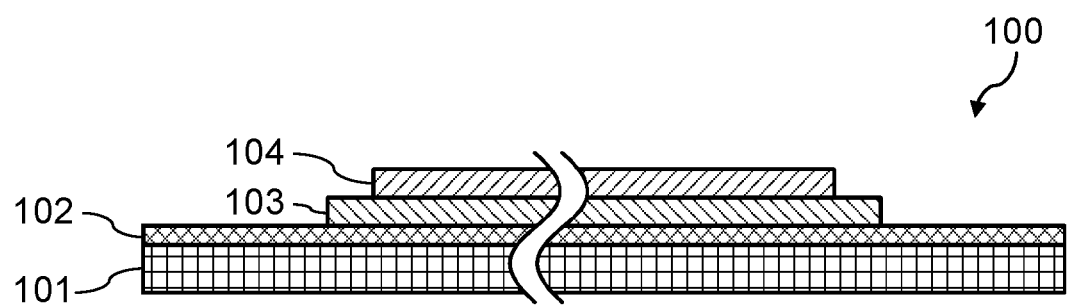
FIG. 1 is a sectional view illustrating a colored sheet.

Also, it should be noted that the following description and the accompanying drawings are provided to allow any person skilled in the art to fully understand the present disclosure, and that it is not intended to limit the subject matter described in the claims by the following description.
Colored Sheet:

FIG. 1 is a sectional view illustrating a colored sheet. It should be noted that the thickness of each layer shown in the figure is expanded for convenience of explanation and does not show an actual thickness ratio.

As shown in FIG. 1, colored sheet 100 is a film-form member which is to be adhered to an object such as human skin or the like to color the object, and comprises support body 101, thin film 102, restriction layer 103, and colored layer 104.

Support Body 101:

Support body 101, which is used when thin film 104 is mounted to an apparatus which forms colored layer 104 or the like, is a thin sheet-shaped member for allowing thin film 102 to be easily handled by a human hand. Also, support body 101 allows colored sheet 100 to be wound into a roll or to be stacked, and also allows one of stacked colored sheets 100 to be pulled out.

The material forming support body 101 may not particularly be limited and may be any material as far as thin film 102 held on support body can be peeled off. In the present exemplary embodiment, since thin film 102 is made of such a material that increases its separability by presence of water at the boundary with support body 101, support body 101 may preferably be made of a material into which water can penetrate such, for example, as a non-woven fabric or a woven fabric. Specifically, support body 101 may be made, for example, of paper, which is a non-woven fabric of cellulose, and may also be made of a fiber of polyethylene terephthalate, nylon, polyester, polypropylene, or the like.

Also, support body 101 may not necessarily be made of a single material. but may be made of plural materials. Specifically, support body 101 can be made, for example, of a combination of cellulose and polyethylene. This combination can increase the strength of support body 101. Also, support body 101 may not be limited to a fiber body. That is, support body 101 may be a resin or glass body which is hydrophilic on a surface in contact with thin film 102. Also, support body 101 may be configured such that a surface in contact with thin film 102 is made of a fiber and that a non-fabric film is formed on a surface which is not in contact with thin film 102.

The thickness of support body 101 may not particularly be limited and, although it depends on the material used, may, for example, be a thickness selected within a range from 0.05 mm to 0.5 mm Thin Film 102:

Thin film 102 is a member which is peelably held on support body 101 and colored by an inkjet or the like to serve as a base material of an adhesive sheet that is to be adhered to an object. The material for forming thin film 102 may not particularly be limited. In the present exemplary embodiment, since thin film 102 is adhered to a surface of human skin, it is preferable that thin film 102 has flexibility and adhesion so as to fit to the shape of the portion to which it is adhered. Also, thin film 102 may preferably have a high-level safety for a human body. For example, the material for forming thin film 102 may be a polymeric material such, for example, as polylactic acid, polyglycolic acid, or a copolymer of a monomer such, for example, as lactic acid or glycol and another kind of monomer. Especially, thin film 102 made of polylactic acid is preferable, because it can be easily peeled off from support body 101 by soaking support body 101 made of cellulose with water. Also, the structure of thin film 102 may be a film structure, a structure having fine pores or a mesh pattern, or a fiber sheet configured by piled fibers.

Thin film 102 may preferably be such that its presence is not obvious when it is adhered to an object, and thus may preferably have a nano-level thickness. Such nano-level thin film 102 may hardly interfere the color of colored layer 104 even if the material forming thin film 102 is not perfectly transparent, so that it is possible to suppress a feeling of strangeness caused by the presence of thin film 102. Specifically, the film thickness of thin film 102 may preferably be selected within a range from 50 nm to 400 nm. Because, thin film 102 having a film thickness smaller than 50 nm may hardly be adhered to an object while keeping its shape, and thin film 102 having a thickness larger than 400 nm may lose flexibility and may be easily observed by other's eyes. In a case where the material forming thin film 102 is polylactic acid, the film thickness may preferably be selected within a range from 150 nm to 300 nm.

Figure 2:
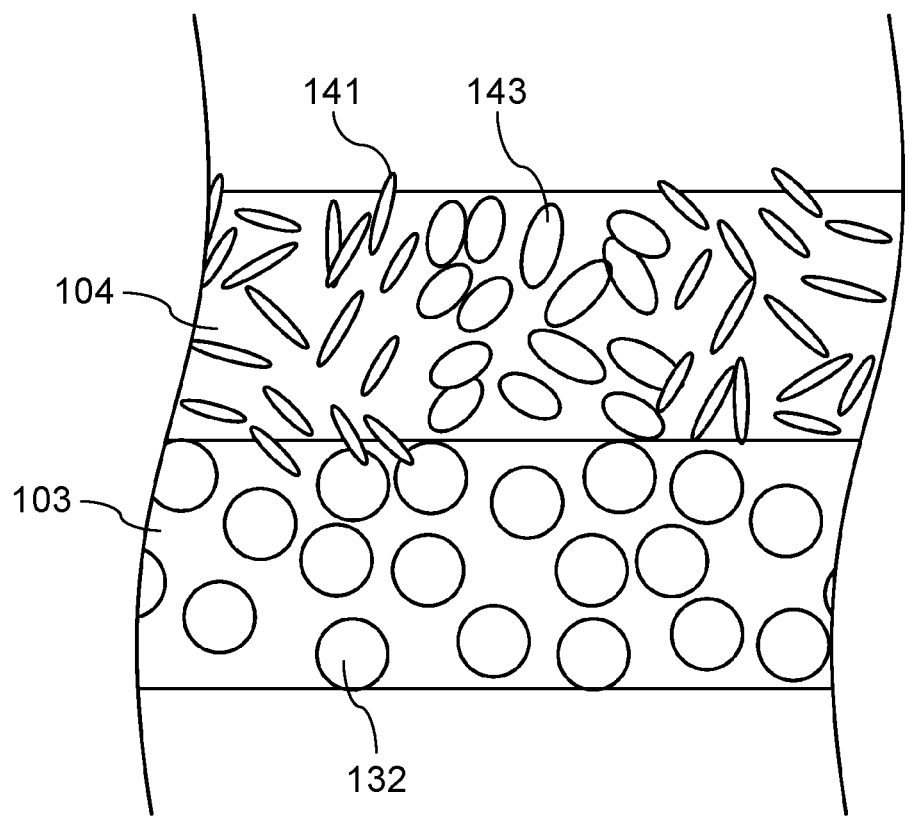
FIG. 2 is a sectional view illustrating a restriction layer and a colored layer.

Restriction Layer 103:

FIG. 2 is a sectional view illustrating a restriction layer and a colored layer.

Restriction layer 103 is a layer which serves as a base when thin film 102 held on support body 101 is colored. Restriction layer 103 is disposed to be in contact with thin film 102. Also, restriction layer 103 contains second microparticles 132 each having a spherical shape, which is difficult to penetrate into support body 101 during coating. Restriction layer 103 disposed on the surface of thin film 102 functions as a barrier layer that prevent contents of colored layer 104 from penetrating through thin film 102 into support body 101.

Here, the term "spherical" used in the specification and claims means to include not only a perfect sphere microparticle, but also any amorphous microparticles as far as they are difficult to penetrate thin film 102 when restriction layer 103 is formed on the surface of thin film 102. The amorphous microparticle may, for example, be a microparticle having a shape that circumscribes a virtual perfect sphere at three or more points and can be as a whole regarded as a spherical shape even it has a certain degree of irregularity. For example, a microparticle having a parallelepiped or cubic shape, which is a solid shape that circumscribes a perfect sphere at eight points, may be an amorphous microparticle and thus included in the spherical microparticles. Preferable amorphous shapes include, for example, sphere, amygdaloidal shape, botryoidal shape, cristate shape, cube, arborescent shape, dendrite, dodecahedron, drusen shape, enantiomorphic shape, equiaxed shape, foliaceous shape, micaceous shape, plate-like shape, granular shape, hemimorphic crystal, skeleton crystal, papillary shape, massive shape, tuberose, trioctahedral crystal, plumose shape, columnar shape, hexagonal symmetry crystal, reniform shape, colloform shape, reticulated shape, rosulate shape, lens-like shape, asteroid shape, and bundle shape.

Although the material forming restriction layer 103 may not particularly be limited, it may preferably be a material that hardly affects the color of colored layer 104. Specifically, restriction layer 103 may be obtained by, for example, coating the surface of thin film 102 with a white pigment by the same method as that for forming colored layer 104.

Also, in the present exemplary embodiment, restriction layer 103 does not cover the whole surface of thin film 102, but it is formed on a part of the surface of thin film 102.

Colored Layer 104:

Colored layer 104 is disposed on restriction layer 103 and contains a large amount of acicular first microparticles 141 which are sharper than second microparticles 132 contained in restriction layer 103. Colored layer 104 is a layer that determines the color of colored sheet 100, or, in other words, determines the color for coloring the object.

Here, the term "acicular" used in the specification and claims means a shape that is easy to penetrate thin film 102 in a case where colored layer 104 is formed on the surface of thin film 102 without any intervening restriction layer 103. Specifically, the acicular shape may, for example, be a shape that circumscribes a virtual perfect sphere at only two points. As specific pigments, particles contained, for example, in a yellow pigment or a red pigment are often acicular particles.

Specifically, colored layer 104 may not be colored entirely uniform, but may be divided in planar view to micro regions each having a different color from another as shown in FIG. 2. That is, colored layer 104 may be configured by first microparticles 141 in some micro regions, and by third microparticles 143 in the other micro regions. In this case, third microparticles 143 may be acicular microparticles sharper than second microparticles 132 or may be spherical microparticles similar in shape to second microparticles 132. Colored layer 104 having this structure allows plural different color regions to be combined, so that the color of colored layer 104 as a whole can be arbitrarily adjusted and that colored sheet 100 can be made to have a gradation or a color-coded pattern.

Although it has been described that colored layer 104 is a layer formed based on pigment containing microparticles in the present exemplary embodiment, colored layer 104 may not be limited to such layer. Colored layer 104 may be formed based on a dye such as an ink or the like. Also, colored layer 104 may not be colored differently on a region by region basis, but it may be colored entirely uniform with an arbitrary color.

Also, in the present exemplary embodiment, restriction layer 103 and colored layer 104 have film thicknesses that are about the same as each other, because they are formed on thin film 102 by the same method. Also, the area in which colored layer 104 is formed is narrower than the area in which restriction layer 104 is formed.

Colored Sheet Manufacturing Method:

Next, a method for manufacturing colored sheet 100 will be described.

Figure 3:
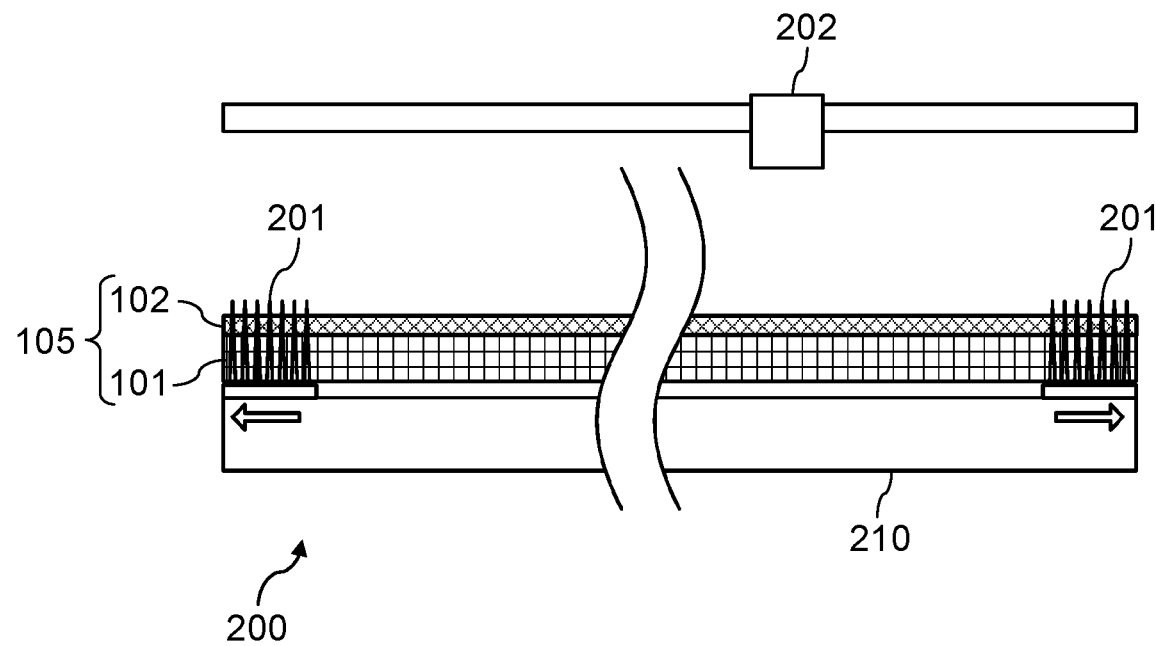
FIG. 3 is a diagram illustrating a state in which a print receiver body is held on a microneedle array in a coating machine.

Holding Step:

First, as shown in FIG. 3, print receiver body 105 comprising support body 101 and thin film 102 is held by piercing print receiver body 105 from the support body 101 side with microneedle arrays 201 in coating machine 200. The diameter of each of microneedles constructing microneedle array 201 may be about 0.15 mm to 0.25 mm. However, the diameter of each microneedle may not be limited to this range, as far as the microneedle is sufficiently fine in a range in which it does not easily break when it penetrates support body 101.

In the present exemplary embodiment, print receiver body 105 is not held by microneedle arrays extending under entire print receiver body 105, but is held at ends of print receiver body 105 by plural microneedle arrays 201 disposed to be apart from each other on stage 210. Microneedle arrays 210 are moved away from each other to take up the slack of print receiver body 105, so that print receiver body 105 is held in a tightly stretched state. This makes it possible to apply a favorable coating to the unwrinkled surface of thin film 102.

Figure 4:
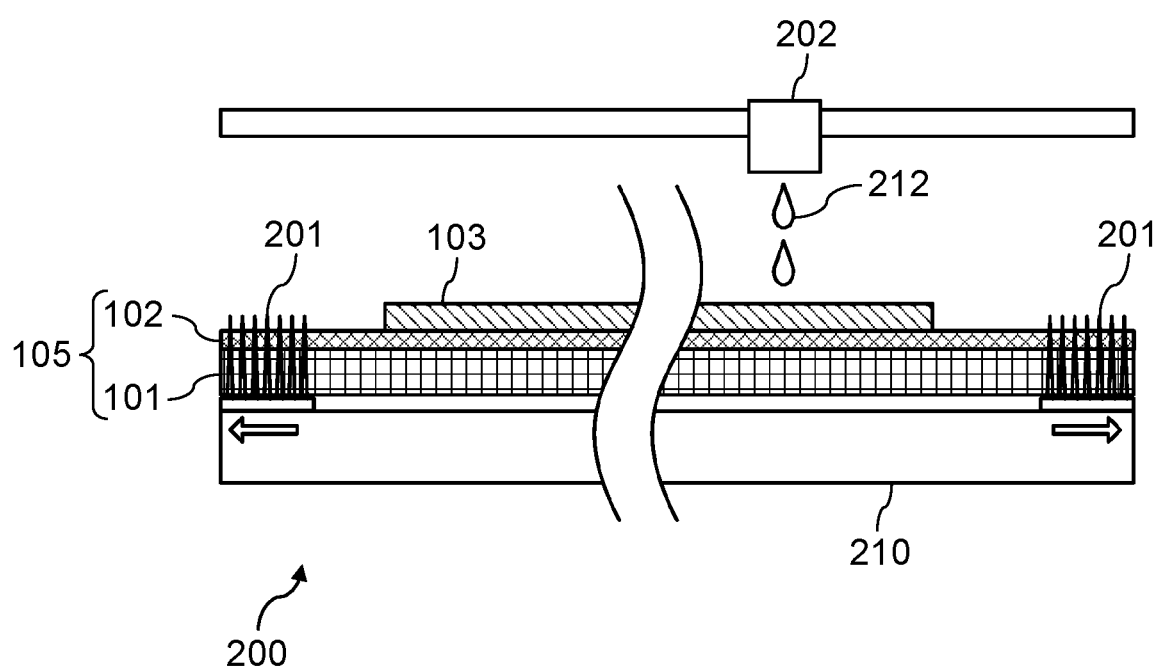
FIG. 4 is a diagram illustrating a state in which a restriction layer is formed by applying a second coating fluid in the coating machine.

Restricting Step:

Next, second coating fluid 212 is applied to the surface of thin film 102 to form restriction layer 103 as shown in FIG. 4. In the present exemplary embodiment, the coating is performed such that droplets of second coating fluid 212 are sprayed onto the surface of thin film 102 with inkjet head 202, while inkjet head 202 is moved relatively to print receiver body 105. Specific coating method may not particularly be limited, the quantity of one droplet delivered from inkjet head 202 may, for example, be about 10 pl, and a desired quantity of fluid (i.e., the film thickness) can be realized by repeating delivery of the droplet onto the same position plural times.

Also, in the present exemplary embodiment, second coating fluid 212 is a white pigment which contains spherical second microparticles 132.

In this manner, by applying second coating fluid 212 onto the same position (area) on the surface of thin film 102 as the position (area) which will be coated with first coating fluid 211 in the next step, it is possible to prevent acicular first microparticles 141 contained in first coating fluid 211 from penetrating thin film 102.

Figure 5:
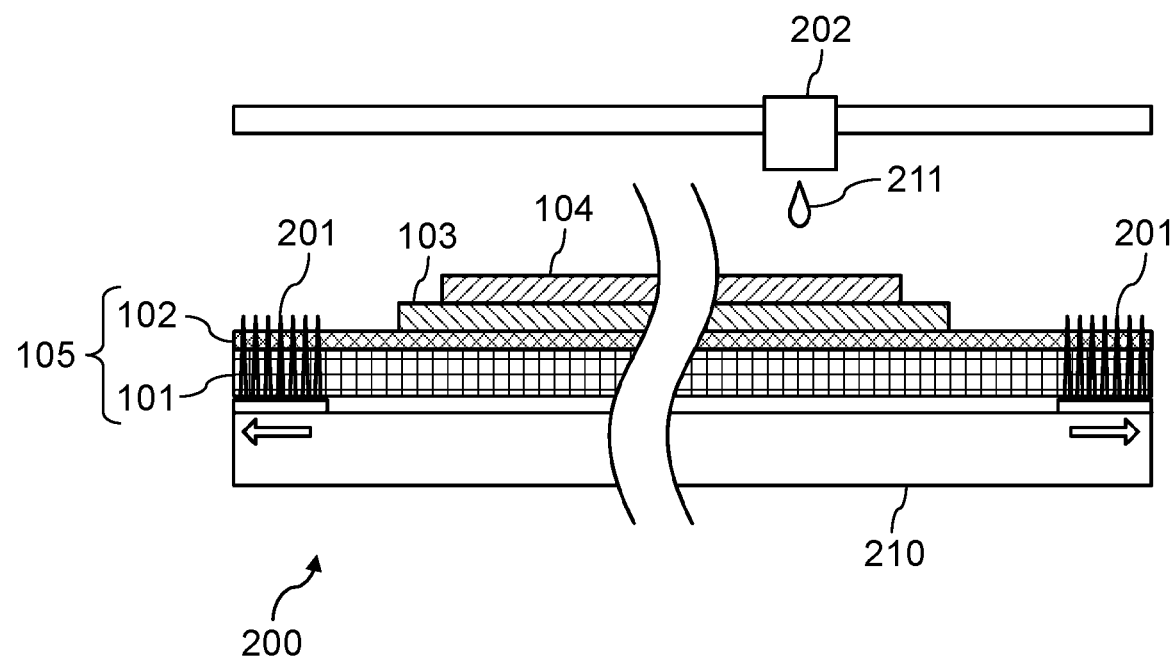
FIG. 5 is a diagram illustrating a state in which a colored layer is formed by applying a first coating fluid in the coating machine.

Coloring Step:

Next, as shown in FIG. 5, first coating fluid 211 is applied to restriction layer 103, or the area which has been coated with second coating fluid 212, to form colored layer 104. In the present exemplary embodiment, in the same manner as the application of second coating fluid 212, the coating is performed such that droplets of first coating fluid 211 are sprayed onto the surface of restriction layer 103 with inkjet head 202 to apply first coating fluid 211 to the thin film 102 side of print receiver body 105, while inkjet head 202 is moved relatively to print receiver body 105.

Also, in the present exemplary embodiment, first coating fluid 211 containing acicular first microparticles 141, third coating fluid (not shown) containing third microparticles 143 which are slightly more rounded than first microparticles 141, and another coating fluid are applied to respective micro regions as shown in FIG. 2 to realize an arbitrary color or a gradation pattern.

In the above-described coating method, it may be preferable that the film thickness of thin film 102 of print receiver body 105 is selected within a range from 50 nm to 400 nm. Because, thin film 102 having a film thickness smaller than 50 nm would be penetrated by first microparticles 141 during the step of forming colored layer 104 to cause bleeding or the like even if restriction layer 103 has been formed, and thin film 102 having a film thickness larger than 400 nm would be hardly penetrated by first microparticles 141 without the need of forming restriction layer 103.

By undergoing the above-described steps, first microparticles 141 are prevented from reaching support body 101, so that it is possible to manufacture colored sheet 100 which has a desired color without bleeding or the like. Further, colored layer 104 is formed by inkjet head 202, it is possible to manufacture colored sheet 100 which is provided with arbitrary color, pattern, characters, or picture.

Also, colored sheet 100 obtained by undergoing the above-described steps has such features that it has a high adhesion to an object such, for example, as human skin, and that thin film 102 is less visible after having been adhered. Further, colored sheet 100 can hide shallow grooves such, for example, as wrinkles appeared on the surface of the object. Further, it is possible by white restriction layer 103 or the like to effectively hide freckles existing on the surface of the object.

How to Use the Colored Sheet:

Colored sheet 100 of the present disclosure can be used, for example, to hide freckles appeared locally on human skin. In this case, support body 101 may be wetted with water to allow thin film 102 to be easily separable, and thin film 102 may be adhered to the freckled portion while peeling thin film 102 from support body 101. This makes it possible to realize coloring of the surface of the object by the adhered sheet (the sheet comprising thin film 102, restriction layer 103 and colored layer 104) having colored layer 104 disposed on the outer aide of the adhered sheet.

Others:

It should be understood that the present disclosure may not be limited to the above-described exemplary embodiment. For example, another embodiment which may be realized by arbitrarily combining the components disclosed in the present specification or by deleting some of the components may also be exemplary embodiment of the present disclosure. Also, various modifications obtained by modifying or changing the disclosed exemplary embodiment within a scope without departing from the meanings of wordings described in the claims may also be included in the present disclosure.

Figure 6:
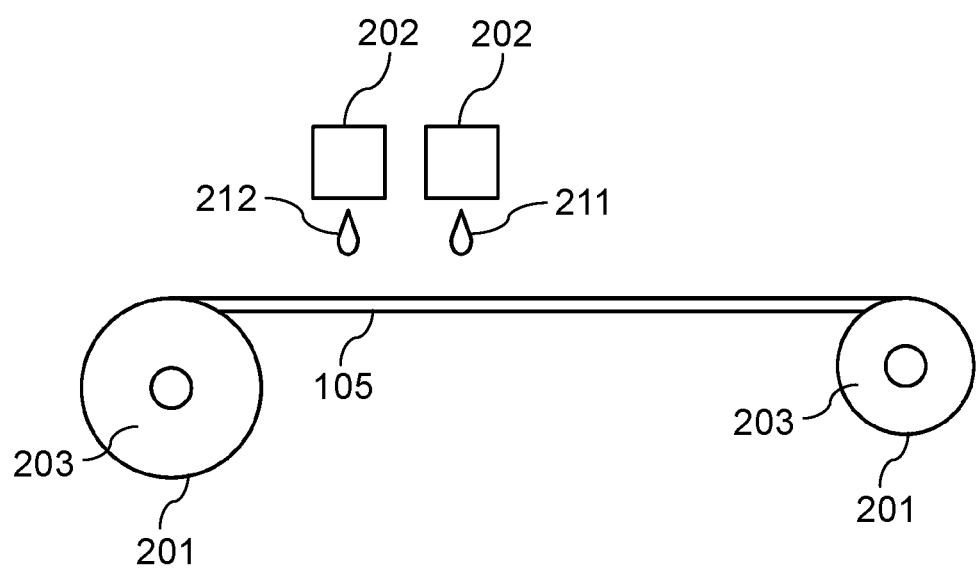
FIG. 6 is a diagram illustrating another example of coating machine.

For example, as shown in FIG. 6, rotational roller 203 provided on its surface with microneedle array 201 having microneedles arranged radially from the rotation axis as a center may be used. While rolled print receiver body 105 is being drawn out by rotating rotational roller 203 in the state microneedle array 201 is stuck to support body 101, print receiver body 105 may be coated with second coating fluid 212 and first coating fluid 211 continuously using plural inkjet heads 202.

Figure 7:
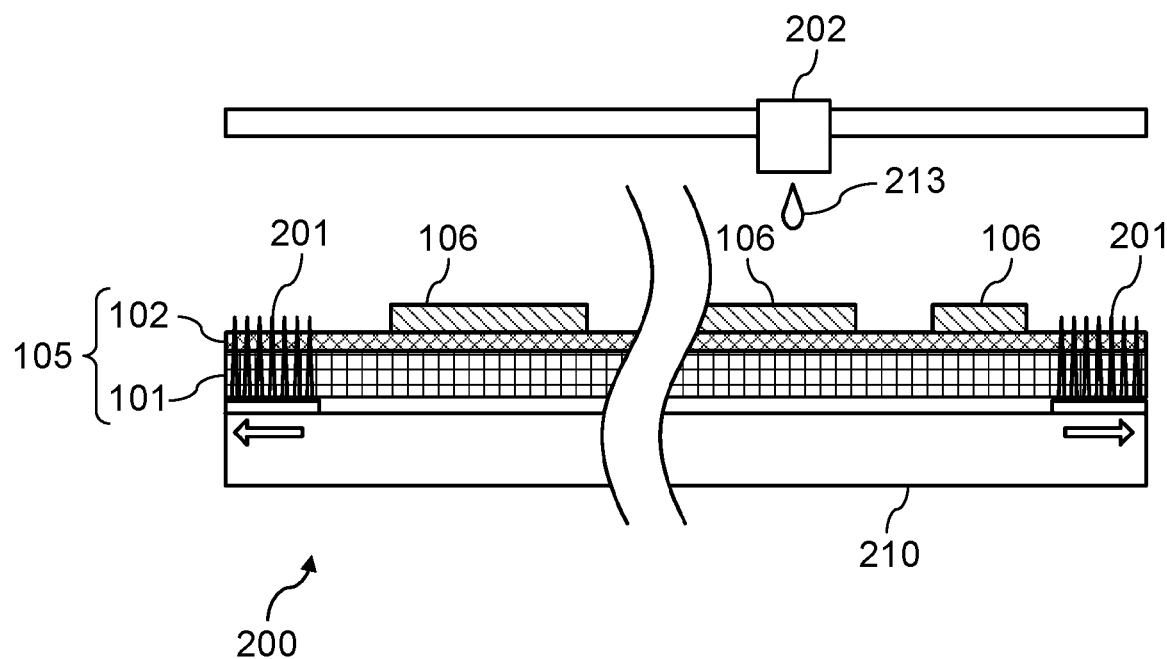
FIG. 7 is a diagram illustrating a state in which an adhesive layer is formed by adhering an adhesive material to the print receiver body in the coating machine.
Figure 8:
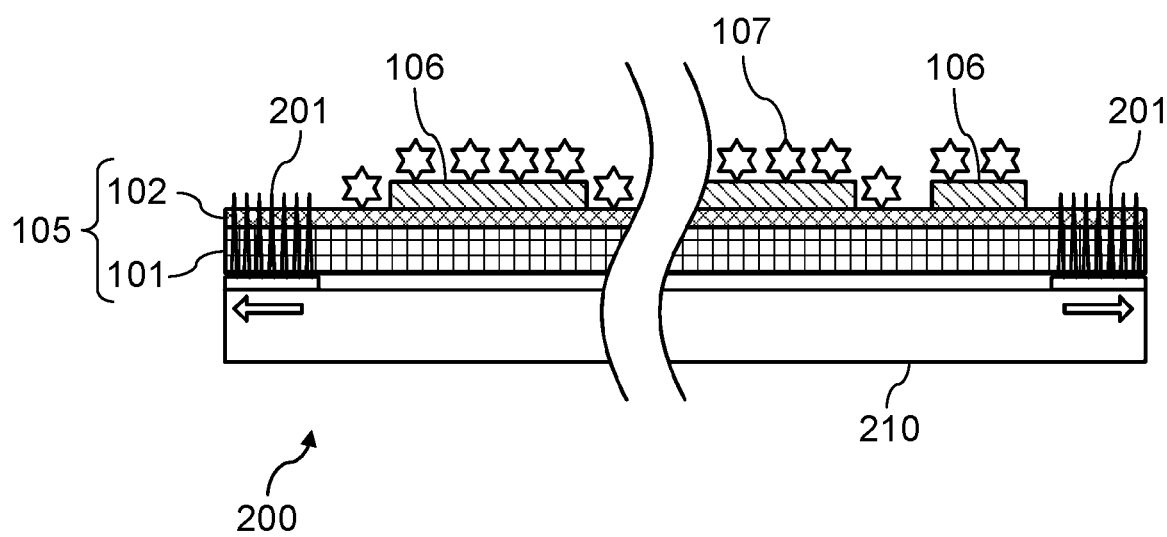
FIG. 8 is a diagram illustrating a state in which flakes are sprinkled from the adhesive layer side in the coating machine.
Figure 9:
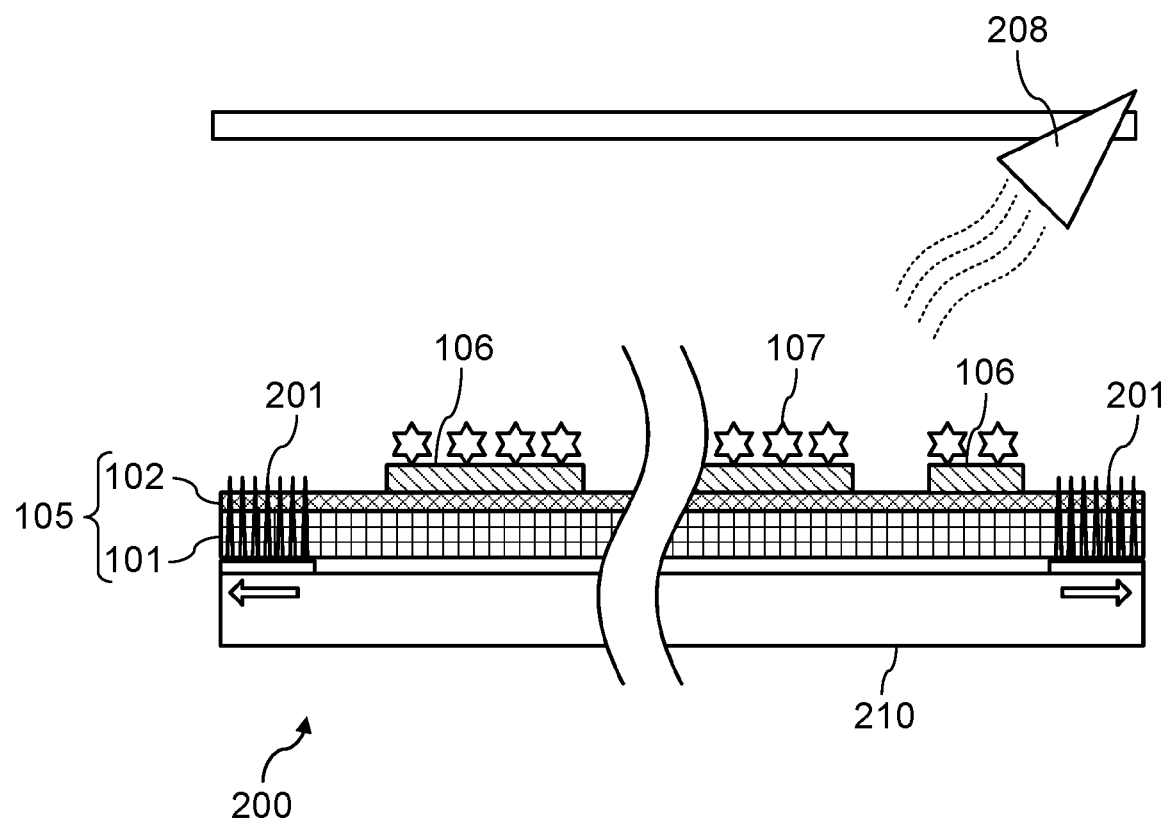
FIG. 9 is a diagram illustrating a state in which flakes accumulated on areas other than a surface of the adhesive layer are removed using a blower in the coating machine.

Also, the method of the present disclosure may be modified as a method for manufacturing a decoration sheet which is adhered to an object to decorate the object. In this method, as shown in FIG. 7, adhesive material 213 is applied by spraying to thin film 102 formed on print receiver body 105 which has sheet-shaped support body 101 and thin film 102 which serves as a base material of an adhesive sheet to be adhered to an object to form a specific pattern of adhesive layer 106. Then, as shown in FIG. 8, flakes 107 such, for example, as lames are sprinkled on the front surface of adhesive layer 106 formed by adhesive material 213. Then, as shown in FIG. 9, flakes 107 such, for example, as lames dropped on the parts other than the surface of adhesive layer 106 may be blown off by wind pressure of blower 208.

With this method, fine flake printing is possible, so that it is possible to decorate a surface of an object by a fine pattern of flakes.

In this case, adhesive layer 106 may be formed on the front surface of colored layer 104.

Also, restriction layer 103 may be formed on the whole surface of thin film 102, and colored layer 104 may be formed on the whole surface of restriction layer 103.

Also, restriction layer 103 may not be white, but may be any color other than white.

Also, colored layer 104 may be formed on a part on which restriction layer 103 has not been formed to intentionally provide thin film 102 with a blurry colored part.

Also, restriction layer 103 may not contain second microparticles 132 as far as it has a strength sufficient to prevent the phenomenon that acicular first microparticles 141 penetrate thin film 102.

Also, print receiver body 105 may not be held by microneedle arrays 201 in coating machine 200, but may be held by a hard support plate having an adhesive surface.

Also, the length of each microneedle of microneedle array 201 may not be the length penetrating through print receiver body 105 as far as it can hold print receiver body 105.

Also, colored sheet 100 may have another layer in addition to restriction layer 103 and colored layer 104 within a scope without departing from the spirit of the present disclosure. For example, colored sheet 100 may be provided with a transparent layer that stabilize colored layer 104.

Also, thin film 102 may not be transparent, but may be colored by an arbitrary method.

Also, the object to be colored by applying colored sheet 100 of the present disclosure may not be limited to human skin.

INDUSTRIAL APPLICABILITY

The colored sheet according to the present disclosure can be used as a sheet for hiding freckles or wrinkles on human skin or for applying a makeup, and also can be used as a sheet for coloring a surface of an object.

REFERENCE MARKS IN THE DRAWINGS 100 colored sheet
101 support body
102 thin film
103 restriction layer
104 colored layer
105 print receiver body
106 adhesive layer
107 flake
132 second microparticle
141 first microparticle
143 third microparticle
200 coating machine
201 microneedle array
202 inkjet head
203 rotational roller
208 blower
210 stage
211 first coating fluid
212 second coating fluid
213 adhesive material

The invention claimed is:

1. A method for manufacturing a colored sheet for coloring an object by adhesion to the object, the method comprising:
   a coloring step of applying by spraying, a first coating fluid containing first microparticles for coloring to a thin film of a print receiver body which has a sheet-shaped support body and the thin film, the thin film being peelably held on the sheet-shaped support body to serve as a base material of an adhesive sheet which is to be adhered to the object; and
   a restricting step of applying by spraying, before the coloring step, a second coating fluid for restricting the first microparticles from penetrating the thin film to a location where the first coating fluid is to be applied.

2. The method for manufacturing the colored sheet according to claim 1, wherein each of the first microparticles has an acicular shape that penetrates the thin film, and
   wherein the second coating fluid contains spherical second microparticles that hardly penetrate the thin film.

3. The method for manufacturing the colored sheet according to claim 1, wherein the thin film is colored white by the second coating fluid.

4. The method for manufacturing the colored sheet according to claim 1, wherein the thin film has a film thickness selected within a range from 50 nm to 400 nm, inclusive.

5. The method for manufacturing the colored sheet according to claim 1, wherein the print receiver body is held by being penetrated with microneedles during the coloring step.

* * * * *